US006585764B2

(12) United States Patent
Wright et al.

(10) Patent No.: US 6,585,764 B2
(45) Date of Patent: Jul. 1, 2003

(54) STENT WITH THERAPEUTICALLY ACTIVE DOSAGE OF RAPAMYCIN COATED THEREON

(75) Inventors: Carol Wright, Somerset, NJ (US); Gerard H. Llanos, Stewartsville, NJ (US); Ronald Rakos, Middlesex County, NJ (US); Kristen King, Hoboken, NJ (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/874,117

(22) Filed: Jun. 4, 2001

(65) Prior Publication Data

US 2001/0027340 A1 Oct. 4, 2001

Related U.S. Application Data

(63) Continuation of application No. 09/061,568, filed on Apr. 16, 1998, now Pat. No. 6,273,913.
(60) Provisional application No. 60/044,692, filed on Apr. 18, 1997.

(51) Int. Cl.[7] .................................................. A61F 2/06
(52) U.S. Cl. ....................................................... 623/1.42
(58) Field of Search ............................. 623/1.15, 1.39, 623/1.42, 1.4; 427/2.1–2.31

(56) References Cited

U.S. PATENT DOCUMENTS

| | | |
|---|---|---|
| 5,234,456 A | 8/1993 | Silvestini |
| 5,282,823 A | 2/1994 | Schwartz et al. |
| 5,283,257 A | 2/1994 | Gregory et al. |
| 5,288,711 A | 2/1994 | Mitchell et al. |
| 5,342,348 A | 8/1994 | Kaplan |
| 5,383,928 A | 1/1995 | Scott et al. |
| 5,443,496 A | 8/1995 | Schwartz et al. |
| 5,449,382 A | 9/1995 | Dayton |
| 5,464,450 A | 11/1995 | Buscemi et al. |
| 5,464,650 A | 11/1995 | Berg et al. |
| 5,500,013 A | 3/1996 | Buscemi et al. |
| 5,510,077 A | 4/1996 | Dinh et al. |

(List continued on next page.)

FOREIGN PATENT DOCUMENTS

| | | |
|---|---|---|
| EP | 0 712 615 | 5/1996 |
| EP | 0 716 836 | 6/1996 |
| EP | 0 761 251 | 3/1997 |
| EP | 0 850 651 | 7/1998 |
| EP | 0 938 878 A3 | 9/1999 |
| EP | 0 938 878 A2 | 9/1999 |
| WO | WO96/32907 | 10/1996 |
| WO | WO97/33534 A1 | 9/1997 |
| WO | WO98/23228 | 6/1998 |
| WO | WO98/34669 | 8/1998 |
| WO | WO98/47447 A1 | 10/1998 |
| WO | WO98/56312 | 12/1998 |

OTHER PUBLICATIONS

Marx, Steven O. et al., Rapamycin–FKBP Inhibits Cell Cycle Regulators of Proliferation in Vascular Smooth Muscle Cells, Circulation Research, 1995;76(3):412–417.
Serruys, Patrick W. et al., Heparin–Coated Palmaz–Schatz Stents in Human Coronary Arteries, Circulation. 1996;93;412–422.
Lundergan, Conor F., MD et al., Peptide Inhibition of Myointimal Proliferation by Angiopeptin, a Somatostatin Analogue, JACC vol. 17, No. 6, May 1991:132B–6B.

(List continued on next page.)

Primary Examiner—David H. Willse
Assistant Examiner—Suzette J. Jackson
(74) Attorney, Agent, or Firm—Paul A. Coletti

(57) ABSTRACT

Delivery of rapamycin locally, particularly from intravascular stent, directly from micropores in the stent body or mixed or bound to a polymer coating applied on stent, to inhibit neointimal tissue proliferation and thereby prevent restenosis. This invention also facilitates the performance of the stent in inhibiting restenosis.

20 Claims, 2 Drawing Sheets

U.S. PATENT DOCUMENTS

| | | |
|---|---|---|
| 5,516,781 A | 5/1996 | Morris et al. |
| 5,545,208 A | 8/1996 | Wolff et al. |
| 5,551,954 A | 9/1996 | Buscemi et al. |
| 5,554,182 A | 9/1996 | Dinh et al. |
| 5,562,922 A | 10/1996 | Lambert |
| 5,563,146 A | 10/1996 | Morris et al. |
| 5,571,166 A | 11/1996 | Dinh et al. |
| 5,578,075 A | 11/1996 | Dayton |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,605,696 A | 2/1997 | Eury et al. |
| 5,607,463 A | 3/1997 | Schwartz et al. |
| 5,607,475 A | 3/1997 | Cahalan et al. |
| 5,609,629 A | 3/1997 | Feamot et al. |
| 5,624,411 A | 4/1997 | Tuch |
| 5,628,785 A | 5/1997 | Schwartz et al. |
| 5,629,077 A | 5/1997 | Turnlund et al. |
| 5,632,840 A | 5/1997 | Campbell |
| 5,637,113 A | 6/1997 | Tartaglia et al. |
| 5,646,160 A | 7/1997 | Morris et al. |
| 5,649,977 A | 7/1997 | Campbell |
| 5,651,174 A | 7/1997 | Schwartz et al. |
| 5,665,591 A * | 9/1997 | Sonenshein et al. ........ 435/375 |
| 5,672,638 A | 9/1997 | Verhoeven et al. |
| 5,674,242 A | 10/1997 | Phan et al. |
| 5,679,400 A | 10/1997 | Tuch |
| 5,679,659 A | 10/1997 | Verhoeven et al. |
| 5,693,085 A | 12/1997 | Buirge et al. |
| 5,697,967 A | 12/1997 | Dinh et al. |
| 5,700,286 A | 12/1997 | Tartaglia et al. |
| 5,707,385 A | 1/1998 | Williams |
| 5,725,567 A | 3/1998 | Wolff et al. |
| 5,728,150 A | 3/1998 | McDonald et al. |
| 5,728,420 A | 3/1998 | Keogh |
| 5,733,327 A | 3/1998 | Igaki et al. |
| 5,735,897 A | 4/1998 | Buirge |
| 5,755,772 A | 5/1998 | Evans et al. |
| 5,769,883 A | 6/1998 | Buscemi et al. |
| 5,776,184 A | 7/1998 | Tuch |
| 5,782,908 A | 7/1998 | Cahalan et al. |
| 5,788,979 A | 8/1998 | Alt et al. |
| 5,799,384 A | 9/1998 | Schwartz et al. |
| 5,800,507 A | 9/1998 | Schwartz |
| 5,820,917 A | 10/1998 | Tuch |
| 5,820,918 A | 10/1998 | Ronan et al. |
| 5,824,048 A | 10/1998 | Tuch |
| 5,824,049 A | 10/1998 | Ragheb et al. |
| 5,833,651 A | 11/1998 | Donovan et al. |
| 5,837,008 A | 11/1998 | Berg et al. |
| 5,837,313 A | 11/1998 | Ding et al. |
| 5,843,172 A | 12/1998 | Yan |
| 5,849,034 A | 12/1998 | Schwartz |
| 5,851,217 A | 12/1998 | Wolff et al. |
| 5,851,231 A | 12/1998 | Wolff et al. |
| 5,865,814 A | 2/1999 | Tuch |
| 5,871,535 A | 2/1999 | Wolff et al. |
| 5,879,697 A | 3/1999 | Ding et al. |
| 5,882,335 A | 3/1999 | Leone et al. |
| 5,893,840 A * | 4/1999 | Hull et al. ..................... 604/96 |
| 5,932,243 A * | 8/1999 | Fricker et al. .............. 424/450 |
| 5,968,091 A * | 10/1999 | Pinchuk et al. ............ 623/1.15 |
| 6,015,432 A * | 1/2000 | Rakos et al. ............... 623/1.15 |
| 6,153,252 A * | 11/2000 | Hossainy et al. ............ 427/2.3 |
| 6,273,913 B1 * | 8/2001 | Wright et al. .............. 623/1.42 |
| 6,369,039 B1 * | 4/2002 | Palasis et al. ................. 514/44 |

OTHER PUBLICATIONS

Liu, Ming Wei, MD et al., Restenosis After Coronary Angioplasty Potential Biologic Determinants and Role of Intimal Hyperplasia, Circulation 1989, 79;1374–1387.

Serruys, P. W. et al., Evaluation of Ketanserin in the Prevention of Restenosis After Percutaneous Transluminal Coronary Angioplasty –A Multicenter Randomized Double–Blind Placebo–Controlled Trial, Circulation vol. 88, No. 4, Part 1, Oct. 1993; 1588–1601.

Berk, Bradford C. MD et al., Pharmacologic Roles of Heparin and Glucocorticoids to Prevent Restenosis After Coronary Angioplasty, JACC vol. 17, No. 6, May 1991;111B–7B.

Serruys, Patrick W. MD et al. A Comparison of Balloon–xpandable–Stent Implantation with Balloon Angioplasty in Patients with Coronary Artery Disease. The New England Journal of Medicine, vol. 331, No. 8, Aug. 25, 1994, 489–495.

Fischman, David L. MD et al., A Randomized Comparison of Coronary–Stent Placement and Balloon Angioplasty in Patients with Coronary Artery Disease. The New England Journal of Medicine, vol. 331, No. 8, Aug. 25, 1994, 496–501.

Colburn Michael D. MD et al., Dose Responsive suppression of myointimal hyperlesia by dexemethasone, Journal of Vascular Surgery, vol. 15, No. 3, Mar. 1992, 510–518.

Liu Ming, W. MD, Trapidil in Preventing Restenosis After Balloon Angioplasty in the Atherosclerotic Rabbit, Circulation, vol. 81, No. 3, Mar. 1990, 1089–1093.

Hansson, Goran K. MD, et al., Interferon–Inhibits Arterial Stenosis After Injury, Circulation, vol. 84, No. 3, Sep. 1991, 1266–1272.

Snow, Alan D. et al., Heparin Modulates the Composition of th Extracellular Matrix Domain Surrounding Arterial Smooth Muscle Cells, American Journal of Pathology, vol. 137, No. 2, Aug. 1990, 313–330.

Popma, Jeffrey J. MD et al., Clinical Trials of Restenosis After Coronary Angioplasty, Circulation vol. 84, No. 3, Sep. 1991, 1426–1436.

Campbell, Gordon R. et al., Phenotypic Modulation of Smooth Muscle Cells in Primary Culture, Vascular Smooth Muscle Cells in Culture, CRC Press 1987, pp. 39–55.

Clowes, Alexander W. et al., Significance of Quiescent Smooth Muscle Migration in the Injured Rat Carotid Artery. Cir Res 58: 139–145 1985.

Lange, Richard A. MD et al., Restenosis After Coronary Balloon Angioplasty, Annu. Rev. Med. 1991, 42:127–132.

Franklin, Stephen, M. MD et al., Pharmacologic prevention of restenosis after coronary angioplasty: review of the randomized clinical trials, Coronary Artery Disease, Mar. 1993, vol. 4, No. 3, 232–242.

Suppression by heparin of smooth cell proliferation in injured arteries. Nature, vol. 265, Feb. 17, 1977, 625–626.

Guyton, John, R. et al., Inhibition of Rat Arterial Smooth Muscle Cell Proliferation by Heparin. Circulation Research, vol. 48, No. 5, May 1980, 625–634.

Clowes, Alexander W. et al., Kinetics of Cellular Proliferation after Arterial Injury, Circulation Reseach, vol. 58, No. 6, Jun. 1988, 839–845.

Majesky, Mark W., et al., Heparin Regulates Smooth Muscle S Phase Entry in the Injured Rat Carotid Artery. Circulation Research, vol. 61, No. 2, Aug. 1987, 296–300.

Okada, Tomohisa, MD et al., Localized Release of Perivascular Heparin Inhibits Intimal Proliferation after Endothelial Injury without Systemic Anticoagulation, Neurosurgery, vol. 25, No. 6, 1989, 892–898.

Vasey, Charles G. et al., Clinical Cardiology, Stress Echo and Coronary Flow, Supplement II Circulation, vol. 80, No. 4, Oct. 1989, II–66.

Powell, Jerry S., et al., Inhibitors of Angiotensin–Converting Enzyme Prevent Myointimal Proliferation After Vascular Injury, Science, vol. 245, Jul. 14, 1989, 186–188.

Jonasson, Lena et al., Cyclosporin A Inhibits smooth muscle proliferation in the vascular response to injury. Proc. Natl. Acad. Sci USA 85 (1988), pp. 2303–2308.

Nemecek, Georgina M. et al., Terbinafine Inhibits the Mitogenic Response to Platelet–Derived Growth Factor in Vitro and Neointimal Proliferation in Vivo. The Journal of Pharmacology and Experimental Therapeutics, vol. 248, No. 3, 1998, 1167–1174.

Siekierka, John J., Probing T–Cell Signal Transduction Pathways with the Immunosuppressive Drugs, FK–506 and Rapamycin, Immunologic Research 1994, 13:110–116.

Poon, Michael et al., Rapamycin Inhibits Vascular Smooth Muscle Cell Migration. J. Clin. Invest., vol. 98, No. 10, Nov. 1996, 2277–2283.

Gregory, Clare R. et al., Rapamycin Inhibits Arterial Intimal Thickening Caused by Both AlloImmune and Mechanical Injury, Transplantation vol. 55, No. 6, Jun. 1993, 1409–1418.

* cited by examiner

STENT WITH THERAPEUTICALLY ACTIVE DOSAGE OF RAPAMYCIN COATED THEREON

CROSS REFERENCE TO RELATED APPLICATIONS

This application is a continuation application of U.S. application Ser. No. 09/061,568, filed Apr. 16, 1998, now issued as U.S. Pat. No. 6,273,913, which claims the benefit of U.S. Provisional Application No. 60/044,692, filed Apr. 18, 1997.

FIELD OF THE INVENTION

Delivery of rapamycin locally, particularly from an intravascular stent, directly from micropores in the stent body or mixed or bound to a polymer coating applied on stent, to inhibit neointimal tissue proliferation and thereby prevent restenosis. This invention also facilitates the performance of the stent in inhibiting restenosis.

BACKGROUND OF THE INVENTION

Re-narrowing (restenosis) of an artherosclerotic coronary artery after percutaneous transluminal coronary angioplasty (PTCA) occurs in 10–50% of patients undergoing this procedure and subsequently requires either further angioplasty or coronary artery bypass graft. While the exact hormonal and cellular processes promoting restenosis are still being determined, our present understanding is that the process of PTCA, besides opening the artherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3–6 months results in the filling in and narrowing of the vascular space sufficient to significantly obstruct coronary blood flow.

Several recent experimental approaches to preventing SMC proliferation have shown promise althrough the mechanisms for most agents employed are still unclear. Heparin is the best known and characterized agent causing inhibition of SMC proliferation both in vitro and in animal models of balloon angioplasty-mediated injury. The mechanism of SMC inhibition with heparin is still not known but may be due to any or all of the following: 1) reduced expression of the growth regulatory protooncogenes c-fos and c-myc, 2) reduced cellular production of tissue plasminogen activator; are 3) binding and dequestration of growth regulatory factors such as fibrovalent growth factor (FGF).

Other agents which have demonstrated the ability to reduce myointimal thickening in animal models of balloon vascular injury are angiopeptin (a somatostatin analog), calcium channel blockers, angiotensin converting enzyme inhibitors (captopril, cilazapril), cyclosporir A, trapidil (an antianginal, antiplatelet agent), terbinafine (antifungal), colchicine and taxol (antitubulin antiproliferatives), and c-myc and c-myb antinsense oligonucleotides.

Additionally, a goat antibody to the SMC mitogen platelet derived growth factor (PDGF) has been shown to be effective in reducing myointimal thickening in a rat model of balloon angioplasty injury, thereby implicating PDGF directly in the etiology of restenosis. Thus, while no therapy has as yet proven successful clinically in preventing restenosis after angioplasty, the in vivo experimental success of several agents known to inhibit SMC growth suggests that these agents as a class have the capacity to prevent clinical restenosis and deserve careful evaluation in humans.

Coronary heart disease is the major cause of death in men over the age of 40 and in women over the age of fifty in the western world. Most coronary artery-related deaths are due to atherosclerosis. Atherosclerotic lesions which limit or obstruct coronary blood flow are the major cause of ischemic heart disease related mortality and result in 500,000–600,000 deaths in the United States annually. To arrest the disease process and prevent the more advanced disease states in which the cardiac muscle itself is compromised, direct intervention has been employed via percutaneous transluminal coronary angioplasty (PTCA) or coronary artery bypass graft (CABG).

PTCA is a procedure in which a small balloon-tipped catheter is passed down a narrowed coronary artery and then expanded to re-open the artery. It is currently performed in approximately 250,000–300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute reocclusion) and in the long term (restenosis).

The mechanism of acute reocclusion appears to involve several factors and may result from vascular recoil with resultant closure of the artery and/or deposition of blood platelets along the damaged length of the newly opened blood vessel followed by formation of a fibrin/red blood cell thrombus. Recently, intravascular stents have been examined as a means of preventing acute reclosure after PTCA.

Restenosis (chronic reclosure) after angioplasty is a more gradual process than acute reocclusion: 30% of patients with subtotal lesions and 50% of patients with chronic total lesions will go on to restenosis after angioplasty. While the exact mechanism for restenosis is still under active investigation, the general aspects of the restenosis process have been identified.

In the normal arterial will, smooth muscle cells (SMC) proliferate at a low rate (<0.1%/day; ref). SMC in vessel wall exists in a 'contractile' phenotype characterized by 80–90% of the cell cytoplasmic volume occupied with the contractile apparatus. Endoplasmic reticulum, golgi bodies, and free ribosomes are few and located in the perinuclear region. Extracellular matrix surrounds SMC and is rich in heparin-like glycosylaminoglycans which are believed to be responsible for maintaining SMC in the contractile phenotypic state.

Upon pressure expansion of an intracoronary balloon catheter during angioplasty, smooth muscle cells within the arterial wall become injured. Cell derived growth factors such as platelet derived growth factor (PDGF), basic fibroblast growth factor (bFGF), epidermal growth factor (EGF), etc. released from platelets (i.e., PDGF) adhering to the damaged arterial luminal surface, invading macrophages and/or leukocytes, or directly from SMC (i.e., BFGF) provoke a proliferation and migratory response in medial SMC. These cells undergo a phenotypic change from the contractile phenotyope to a 'synthetic' phenotype characterized by only few contractile filament bundles but extensive rough endoplasmic reticulum, golgi and free ribosomes. Proliferation/migration usually begins within 1–2 days postinjury and peaks at 2 days in the media, rapidly declining thereafter (Campbell et al., In: *Vascular Smooth Muscle Cells in Culture,* Campbell, J. H. and Campbell, G. R., Eds, CRC Press, Boca Ration, 1987, pp. 39–55); Clowes, A. W. and Schwartz, S. M., Circ. Res. 56:139–145, 1985).

Finally, daughter synthetic cells migrate to the intimal layer of arterial smooth muscle and continue to proliferate. Proliferation and migration continues until the damaged luminal endothelial layer regenerates at which time proliferation ceases within the intima, usually within 7–14 days postinjury. The remaining increase in intimal thickening which occurs over the next 3–6 months is due to an increase in extracellular matrix rather than cell number. Thus, SMC migration and proliferation is an acute response to vessel injury while intimal hyperplasia is a more chronic response. (Liu et al., Circulation, 79:1374–1387, 1989).

Patients with symptomatic reocclusion require either repeat PTCA or CABG. Because 30–50% of patients undergoing PTCA will experience restenosis, restenosis has clearly limited the success of PTCA as a therapeutic approach to coronary artery disease. Because SMC proliferation and migration are intimately involved with the pathophysiological response to arterial injury, prevention of SMC proliferation and migration represents a target for pharmacological intervention in the prevention of restenosis.

SUMMARY OF THE INVENTION
Novel Features and Applications to Stent Technology

Currently, attempts to improve the clinical performance of stents have involved some variation of either applying a coating to the metal, attaching a covering or membrane, or embedding material on the surface via ion bombardment. A stent designed to include reservoirs is a new approach which offers several important advantages over existing technologies.

Local Drug Delivery from a Stent to Inhibit Restenosis

In this application, it is desired to deliver a therapeutic agent to the site of arterial injury. The conventional approach has been to incorporate the therapeutic agent into a polymer material which is then coated on the stent. The ideal coating material must be able to adhere strongly to the metal stent both before and after expansion, be capable of retaining the drug at a sufficient load level to obtain the required dose, be able to release the drug in a controlled way over a period of several weeks, and be as thin as possible so as to minimize the increase in profile. In addition, the coating material should not contribute to any adverse response by the body (i.e., should be non-thrombogenic, non-inflammatory, etc.). To date, the ideal coating material has not been developed for this application.

An alternative would be to design the stent to contain reservoirs which could be loaded with the drug. A coating or membrane of biocompatable material could be applied over the reservoirs which would control the diffusion of the drug from the reservoirs to the artery wall.

One advantage of this system is that the properties of the coating can be optimized for achieving superior biocompatibility and adhesion properties, without the addition requirement of being able to load and release the drug. The size, shape, position, and number of reservoirs can be used to control the amount of drug, and therefore the dose delivered.

DESCRIPTION OF THE DRAWINGS

The invention will be better understood in connection with the following figures in which.

DETAILED DESCRIPTION OF THE INVENTION

Figure 1:
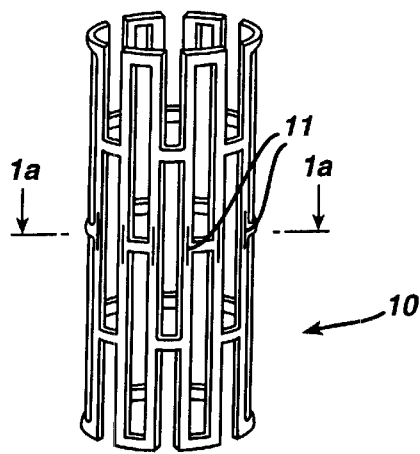
FIGS. 1 and 1*a* are top views and section views of a stent containing reservoirs as described in the present invention.

Pharmacological attempts to prevent restenosis by pharmacologic means have thus far been unsuccessful and all involve systemic administration of the trial agents. Neither aspirin-dipyridamole, ticlopidine, acute heparin administration, chronic warfarin (6 months) nor methylprednisolone have been effective in preventing restenosis although platelet inhibitors have been effective in preventing acute reocclusion after angioplasty. The calcium antagonists have also been unsuccessful in preventing restenosis, although they are still under study. Other agents currently under study include thromboxane inhibitors, prostacyclin mimetics, platelet membrane receptor blockers, thrombin inhibitors and angiotensin converting enzyme inhibitors. These agents must be given systemically, however, and attainment of a therapeutically effective dose may not be possible; antiproliferative (or anti-restenosis) concentrations may exceed the known toxic concentrations of these agents so that levels sufficient to produce smooth muscle inhibition may not be reached (Lang et al., 42 Ann. Rev. Med., 127–132 (1991); Popma et al., 84 *Circulation,* 1426–1436 (1991)).

Additional clinical trials in which the effectiveness for preventing restenosis of dietary fish oil supplements, thromboxane receptor antagonists, cholesterol lowering agents, and serotonin antagonists has been examined have shown either conflicting or negative results so that no pharmacological agents are as yet clinically available to prevent post-angioplasty restenosis (Franklin, S. M. and Faxon, D. P., 4 Coronary Artery Disease, 232–242 (1993); Serruys, P. W. et al., 88 *Circulation,* (part 1) 1588–1601, (1993).

Conversely, stents have proven useful in preventing reducing the proliferation of restenosis. Stents, such as the stent 40, seen in layout in FIG. 4, balloon-expandable slotted metal tubes (usually but not limited to stainless steel), which when expanded within the lumen of an angioplastied coronary artery, provide structural support to the arterial wall. This support is helpful in maintaining an open path for blood flow. In two randomized clinical trials, stents were shown to increase angiographic success after PTCA, increase the stenosed blood vessel lumen and to reduce the lesion recurrence at 6 months (Serruys et al., 331 New Eng Jour. Med, 495, (1994); Fischman et al., 331 New Eng Jour. Med. 496–501 (1994). Additionally, in a preliminary trial, heparin coated stents appear to possess the same benefit of reduction in stenosis diameter at follow-up as was observed with non-heparin coated stents. Additionally, heparin coating appears to have the added benefit of producing a reduction in sub-acute thrombosis after stent implantation (Serruys et al., 93 Circulation, 412–422 (1996). Thus, 1) sustained mechanical expansion of a stenosed coronary artery has been shown to provide some measure of restenosis prevention, and 2) coating of stents with heparin has demonstrated both the feasibility and the clinical usefulness of delivering drugs to local, injured tissue off the surface of the stent.

Numerous agents are being actively studied as antiproliferative agents for use in restenosis and have shown some activity in experimental animal models. These include: heparin and heparin fragments (Clowes and Karnovsky, 265 *Nature,* 25–626, (1977); Guyton, J. R. et. al. 46 Circ. Res., 625–634, (1980); Clowes, A. W. and Clowes, M. M., 52 Lab. Invest., 611–616, (1985) A. W. and Clowes, M. M., 58 Circ. Res., 839–845 (1986); Majesky et al., 61 Circ Res., 296–300, (1987); Snow et al., 137 Am. J. Pathol., 313–330 (1990); Okada, T. et al., 25 *Neurosurgery,* 92–898, (1989) colchicine (Currier, J. W. et al., 80 *Circulation,* 11–66, (1989), taxol (ref), agiotensin converting enzyme (ACE) inhibitors (Powell, J. S. et al., 245 Science, 186–188 (1989), angiopeptin (Lundergan, C. F. et al., 17 Am. J. Cardiol. (Suppl. B); 132B–136B (1991), Cyclosporin A (Jonasson, L. et. al., 85 Proc. Nati, Acad. Sci., 2303 (1988), goat-anti-rabbit PDGF antibody (Ferns, G. A. A., et al., 253 *Science,* 1129–1132 (1991), terbinafine (Nemecek, G. M. et al., 248 J. Pharmacol. Exp. Thera., 1167–11747 (1989), trapidil (Liu, M. W. et al., 81 *Circulation,* 1089–1093 (1990), interferon-gamma (Hansson, G. K. and Holm, 84 *J. Circulation,* 1266–1272 (1991), steroids (Colburn, M. D. et al., 15 J. Vasc. Surg., 510–518 (1992), see also Berk, B. C. et al., 17 J. Am. Coll. Cardiol., 111B–117B (1991), ionizing radiation (ref), fusion toxins (ref) antisense oligonucleotides (ref), gene vectors (ref), and rapamycin (see below).

Of particular interest in rapamycin. Rapamycin is a macrolide antibiotic which blocks IL-2-mediated T-cell proliferation and possesses antiinflammatory activity. While the precise mechanism of rapamycin is still under active investigation, rapamycin has been shown to prevent the $G_1$ to S phase progression of T-cells through the cell cycle by inhibiting specific cell cyclins and cyclin-dependent protein kinases (Siekierka, Immunol. Res. 13: 110–116, 1994). The antiproliferative action of rapamycin is not limited to T-cells; Marx et al. (Circ Res 76:412–417, 1995) have demonstrated that rapamycin prevents proliferation of both rat and human SMC in vitro while Poon et al. have shown the rat, porcine, and human SMC migrating can also be inhibited by rapamycin (J Clin Invest 98: 2277–2283, 1996). Thus, rapamycin is capable of inhibiting both the inflammatory response known to occur after arterial injury and stent implantation, as well as the SMC hyperproliferative response. In fact, the combined effects of rapamycin have been demonstrated to result in a diminished SMC hyperproliferative response in rat femoral artery graft model and in both rat and porcine arterial balloon injury models (Gregory et al., Transplantation 55:1409–1418, 1993; Gallo et al., in press, (1997)). These observations clearly support the potential use of rapamycin in the clinical setting of post-angioplasty restenosis.

Although the ideal agent for restenosis has not yet been identified, some desired properties are clear: inhibition of local thrombosis without the risk systemic bleeding complications and continuous and prevention of the dequale of arterial injury, including local inflammation and sustained prevention smooth muscle proliferation at the site of angioplasty without serious systemic complications. Inasmuch as stents prevent at least a portion of the restenosis process, an agent which prevents inflammation and the proliferation of SMC combined with a stent may provide the most efficacious treatment for post-angioplasty restenosis.

Experiments

Agents: Rapamycin (sirolimus) structural analogs (macrocyclic lactones) and inhibitors of cell-cycle progression.

Delivery Methods:

These can vary:

Local delivery of such agents (rapamycin) from the struts of a stent, from a stent graft, grafts, stent cover or sheath.

Involving comixture with polymers (both degradable and nondegrading) to hold the drug to the stent or graft.

or entrapping the drug into the metal of the stent or graft body which has been modified to contain micropores or channels, as will be explained further herein.

or including covalent binding of the drug to the stent via solution chemistry techniques (such as via the Carmeda process) or dry chemistry techniques (e.g. vapour deposition methods such as rf-plasma polymerization) and combinations thereof.

Catheter delivery intravascularly from a tandem balloon or a porous balloon for intramural uptake Extravascular delivery by the pericardial route Extravascular delivery by the advential application of sustained release formulations.

Uses: for inhibition of cell proliferation to prevent neointimal proliferation and restenosis.

prevention of tumor expansion from stents prevent ingrowth of tissue into catheters and shunts inducing their failure.

1. Experimental Stent Delivery Method—Delivery from Polymer Matrix

Solution of Rapamycin, prepared in a solvent miscible with polymer carrier solution, is mixed with solution of polymer at final concentration range 0.001 weight % to 30 weight % of drug. Polymers are biocompatible (i.e., not elicit any negative tissue reaction or promote mural thrombus formation) and degradable, such as lactone-based polyesters or copolyesters, e.g., polylactide, polycaprolactonglycolide,polyorthoesters, polyanhydrides; polyaminoacids; polysaccharides; polyphosphazenes; poly (ether-ester) copolymers, e.g., PEO-PLLA, or blends thereof. Nonabsorbable biocompatible polymers are also suitable candidates. Polymers such as polydimethylsiolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters.

Polymer/drug mixture is applied to the surfaces of the stent by either dip-coating, or spray coating, or brush coating or dip/spin coating or combinations thereof, and the solvent allowed to evaporate to leave a film with entrapped rapamycin.

2. Experimental Stent Delivery Method—Delivery from Microporous Depots in Stent Through a Polymer Membrane Coating:

Stent, whose body has been modified to contain micropores or channels is dipped into a solution of Rapamycin, range 0.001 wt % to saturated, in organic solvent such as acetone or methylene chloride, for sufficient time to allow solution to permeate into the pores. (The dipping solution can also be compressed to improve the loading efficiency.) After solvent has been allowed to evaporate, the stent is dipped briefly in fresh solvent to remove excess surface bound drug. A solution of polymer, chosen from any identified in the first experimental method, is applied to the stent as detailed above. This outerlayer of polymer will act as diffusion-controller for release of drug.

3. Experimental Stent Delivery Method—Delivery Via Lysis of a Covalent Drug Tether Rapamycin is modified to contain a hydrolytically or enzymatically labile covalent bond for attaching to the surface of the stent which itself has been chemically derivatized to allow covalent immobilization. Covalent bonds such as ester, amides or anhydrides may be suitable for this.

4. Experimental Method—Pericardial Delivery

A: Polymeric Sheet Rapamycin is combined at concentration range previously highlighted, with a degradable polymer such as poly(caprolactone-gylcolide) or non-degradable polymer, e.g., polydimethylsiloxane, and mixture cast as a thin sheet, thickness range $10\mu$ to $1000\mu$. The resulting sheet can be wrapped perivascularly on the target vessel. Preference would be for the absorbable polymer.

B: Conformal Coating: Rapamycin is combined with a polymer that has a melting temperature just above 37° C., range 40°–45° C. Mixture is applied in a molten state to the external side of the target vessel. Upon cooling to body temperature the mixture solidifies conformally to the vessel wall. Both non-degradable and absorbable biocompatible polymers are suitable.

Figure 1A:
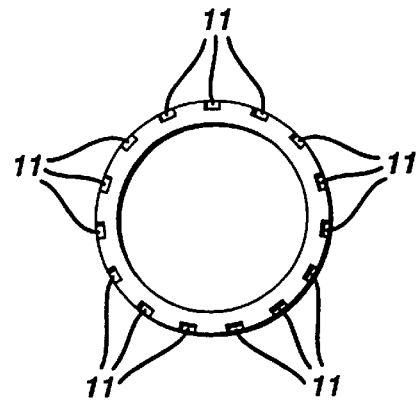
Figure 2A:
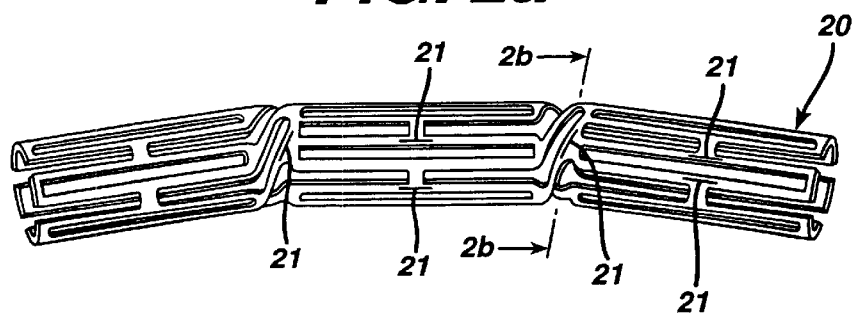
FIGS. 2*a* and 2*b* are similar views of an alternate embodiment of the stent with open ends.
Figure 2B:
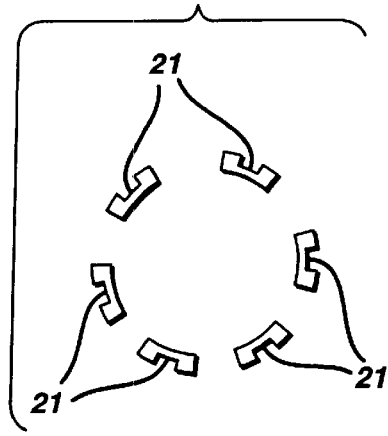
Figure 3A:
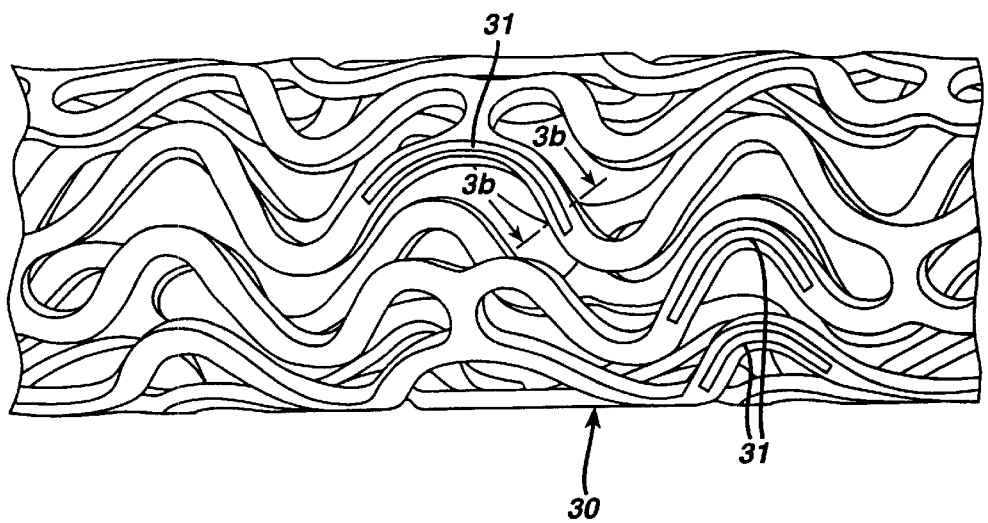
FIGS. 3*a* and 3*b* are further alternate figures of a device containing a grooved reservoir.
Figure 3B:
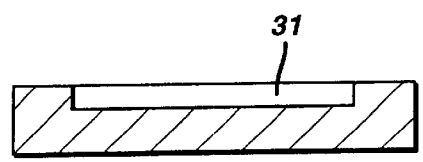
Figure 4:
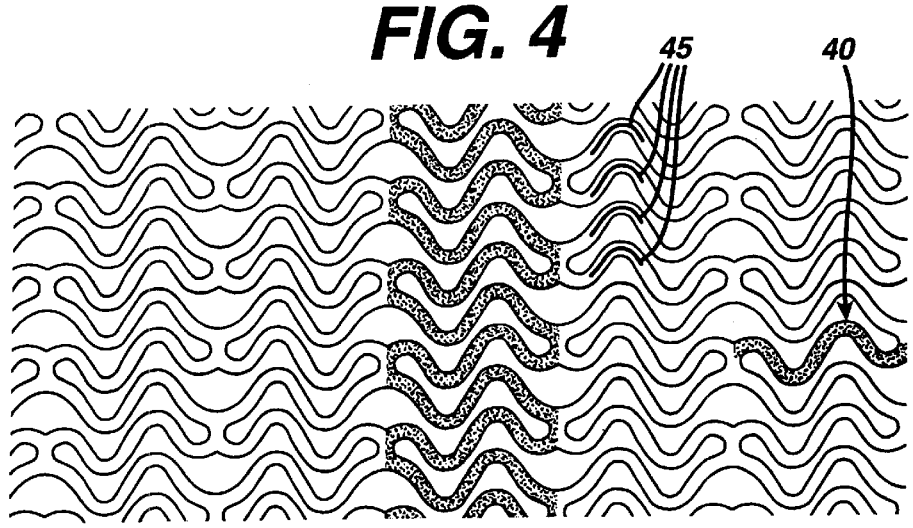
FIG. 4 is a layout view of a device containing a reservoir as in FIG. 3.

As seen in the figures it is also possible to modify currently manufactured stents in order to adequately provide the drug dosages such as rapamycin. As seen in FIGS. 1a, 2a and 3a, any stent strut 10, 20, 30 can be modified to have a certain reservoir or channel 11, 21, 31. Each of these reservoirs can be open or closed as desired. These reservoirs can hold the drug to be delivered. FIG. 4 shows a stent 40 with a reservoir 45 created at the apex of a flexible strut. Of course, this reservoir 45 is intended to be useful to deliver rapamycin or any other drug at a specific point of flexibility of the stent. Accordingly, this concept can be useful for "second generation" type stents.

In any of the foregoing devices, however, it is useful to have the drug dosage applied with enough specificity and enough concentration to provide an effective dosage in the lesion area. In this regard, the reservoir size in the stent struts must be kept at a size of about 0.0005" to about 0.003". Then, it should be possible to adequately apply the drug dosage at the desired location and in the desired amount.

These and other concepts will are disclosed herein. It would be apparent to the reader that modifications are possible to the stent or the drug dosage applied. In any event, however, the any obvious modifications should be perceived to fall within the scope of the invention which is to be realized from the attached claims and their equivalents.

What is claimed is:

1. A stent having a coating containing rapamycin, said coating formed from a polymer mixed carrier containing the rapamycin; and said coating applied to said stent.

2. The stent of claim 1 wherein the stent is dip-coated.

3. The stent of claim 1 wherein the stent is sprayed with said coating.

4. A stent having a coating containing rapamycin or its analogs, wherein said rapamycin or said analogs are contained in the coating at a weight percentage of 0.0001% to 30%.

5. The stent of claim 4 wherein a polymer is mixed to the rapamycin or its analogs.

6. The stent of claim 4 wherein a polymer is bound to the rapamycin or its analogs.

7. The stent of claim 4 wherein the rapamycin or its analogs is entrapped on the surface of the stent by a polymer.

8. A stent having a coating containing rapamycin, said coating formed from a polymer mixed carrier containing the rapamycin or its analogs; and said coating applied to said stent; wherein the polymer is biocompatible and degradable; and wherein the polymer is chosen from: lactone-based polyesters, lactone-based copolyesters; polyanhydrides; polyaminoacids; polysaccharides; polyphosphazenes; poly(ether-ester) copolymers, and blends of such polymers.

9. A stent having a coating containing rapamycin, said coating formed from a polymer mixed carrier containing the rapamycin or its analogs; and said coating applied to said stent; and wherein the polymer is chosen from: lactone-based polyesters, lactone-based copolyesters; polyanhydrides; polyaminoacids; polysaccharides; polyphosphazenes; poly(ether-ester) copolymers, and blends of such polymers.

10. A stent having a coating containing rapamycin, said coating formed from a polymer mixed carrier containing the rapamycin or its analogs; and said coating applied to said stent; wherein the polymer is nonabsorbable; and wherein the polymer is chosen from: polydimethylsiolxane; poly(ethylene)vinylacetate; poly(hydroxy) ethylmethylmethacrylate, polyvinyl pyrrolidone; polytetrafluoroethylene; and cellulose esters.

11. A stent having a coating containing rapamycin or its analogs, said coating formed from a polymer mixed carrier containing the rapamycin or its analogs; and said coating applied to said stent; and wherein the polymer is chosen from: polydimethylsiolxane; poly(ethylene)vinylacetate; poly(hydroxy) ethylmethylmethacrylate, polyvinyl pyrrolidone; polytetrafluoroethylene; and cellulose esters.

12. A stent having a coating containing rapamycin or its analogs, said coating formed from a polymer mixed carrier containing the rapamycin or its analogs; and said coating applied to said stent; and further comprising:

a generally thin walled cylinder, said cylinder containing a plurality of generally solid struts, said applied to said strut, and a channel formed in at least one of said struts, said channel having a closed perimeter on all sides and an open top, and said channel smaller in all dimensions than said strut, said channel containing a reservoir of said rapamycin coating applied therein.

13. A stent having a coating containing rapamycin or its analogs, wherein said rapamycin or said analogs are contained in the coating at a weight percentage of 0.0001% to 30%, wherein the coating is a polymer.

14. The stent of claim 13 wherein said polymer is mixed to the rapamycin or its analogs.

15. The stent of claim 4 wherein said polymer is bound to the rapamycin or its analogs.

16. The stent of claim 13 wherein the rapamycin or its analogs is entrapped on the surface of the stent by said polymer.

17. A stent containing a polymer and rapamycin or its analogs wherein said rapamycin or its analogs are contained in a therapeutically beneficial amount to combat restenosis.

18. The stent of claim 17 wherein said polymer is mixed to the rapamycin or its analogs.

19. The stent of claim 17 wherein said polymer is bound to the rapamycin or its analogs.

20. The stent of claim 17 wherein the rapamycin or its analogs is entrapped on the surface of the stent by said polymer.

* * * * *